United States Patent
Petelle et al.

(10) Patent No.: US 9,095,454 B2
(45) Date of Patent: Aug. 4, 2015

(54) INTRAORAL ORTHOSIS, A METHOD OF FABRICATING SUCH AN ORTHOSIS, AND A METHOD OF ADJUSTING IT

(71) Applicant: PETELLE-FLEURY-RECHERCHES (PFR), Paris (FR)

(72) Inventors: Boris Petelle, Paris (FR); Bernard Fleury, Vincennes (FR)

(73) Assignee: Petelle-Fleury-Recherches (PFR), Paris (FR)

( * ) Notice: Subject to any disclaimer, the term of this patent is extended or adjusted under 35 U.S.C. 154(b) by 194 days.

(21) Appl. No.: 13/644,319

(22) Filed: Oct. 4, 2012

(65) Prior Publication Data
US 2013/0160776 A1 Jun. 27, 2013

(30) Foreign Application Priority Data
Oct. 4, 2011 (FR) ...................................... 11 58946

(51) Int. Cl.
*A61F 5/56* (2006.01)
*A61C 7/36* (2006.01)

(52) U.S. Cl.
CPC . *A61F 5/566* (2013.01); *A61C 7/36* (2013.01); *Y10T 29/4998* (2015.01)

(58) Field of Classification Search
CPC ............ A61F 5/56; A61F 5/566; A61C 7/08; A61C 7/36; A63B 71/085
USPC ........... 128/848, 859–863; 602/902; 433/6, 7, 433/18, 19, 24, 56, 57, 61
See application file for complete search history.

(56) References Cited

U.S. PATENT DOCUMENTS

| 5,409,017 | A | 4/1995 | Lowe |
| 5,820,579 | A | 10/1998 | Plotkin |
| 6,055,986 | A * | 5/2000 | Meade ......................... 128/848 |
| 7,354,270 | B2 | 4/2008 | Abolfathi et al. |
| 8,256,426 | B2 * | 9/2012 | Abramson .................... 128/848 |
| 8,631,800 | B2 * | 1/2014 | Lindsay et al. ............... 128/848 |
| 8,757,164 | B2 * | 6/2014 | Abramson .................... 128/848 |
| 8,783,261 | B2 * | 7/2014 | Thornton ...................... 128/848 |
| 2005/0081859 | A1 | 4/2005 | Scarberry et al. |
| 2011/0036357 | A1 | 2/2011 | Abramson |
| 2012/0145166 | A1 * | 6/2012 | Fallon et al. .................. 128/848 |
| 2013/0263865 | A1 * | 10/2013 | Khast ............................ 128/848 |

FOREIGN PATENT DOCUMENTS

| WO | 97/04716 A1 | 2/1997 |
| WO | 02/38090 A1 | 5/2002 |
| WO | 2006/013238 A1 | 2/2006 |
| WO | 2008/023799 A1 | 2/2008 |

* cited by examiner

*Primary Examiner* — Alireza Nia
*Assistant Examiner* — Raymond E Harris
(74) *Attorney, Agent, or Firm* — Sughrue Mion, PLLC

(57) ABSTRACT

An intraoral orthosis having a first shell and a second shell, the shells being connected together by an adjustable connection device. The adjustable connection device has two notched tabs that are arranged respectively on either side of one of the shells, each notched tab co-operating in adjustable manner with a respective adjustment housing, arranged correspondingly on either side of the other of the shells, each notched tab having adjustment teeth to adjust the position of the shells one relative to the other, and locking housings to lock the position. The locking housings are oriented transversally relative to the adjustment teeth.

18 Claims, 4 Drawing Sheets

INTRAORAL ORTHOSIS, A METHOD OF FABRICATING SUCH AN ORTHOSIS, AND A METHOD OF ADJUSTING IT

FIELD OF THE INVENTION

The present invention relates to an intraoral orthosis, and more particularly to such an orthosis for treating snoring and sleep-apnea syndrome. The present invention also relates to a method of fabricating such an intraoral orthosis and to a method of adjusting it.

BACKGROUND OF THE INVENTION

Intraoral orthoses for treating snoring and sleep apnea are known in the prior art. Such orthoses generally comprise a maxillary splint and a mandibular splint that are connected together by a connection device that makes it possible to adjust the position of the mandibular splint relative to the maxillary splint. It has been observed that, for most people, there exists a jaw position in which snoring and apnea decrease or cease. This position differs depending on the user, and it is thus necessary to determine, with accuracy, the correct position, so as to be able to adjust the orthosis for each user. Documents WO 97/04716, U.S. Pat. No. 5,409,017, U.S. Pat. No. 5,820,579, WO 02/38090, WO 2006/013238, U.S. 2011/0036357, U.S. Pat. No. 7,354,270, U.S. 2005/0081859, and WO 2008/023799 describe prior-art devices. Such devices present a certain number of drawbacks. Thus, it is generally quite complex to adapt and adjust splints and their positions and this needs to be performed by a specialist. This requires numerous visits and thus presents a significant cost. In addition, in order for an orthosis to be properly fitted to its user, it is generally necessary to make molds of the user's teeth so that the splints can then be made to measure in a laboratory as a function of the molds. The qualities required for an orthosis are, in particular, compactness so as to limit discomfort, and satisfactory retention of the splints on the dental arches, in particular so as to be certain of the absence of nocturnal mismatching, resulting in a loss of effectiveness. In addition, it is desirable for the splint connection system to be capable of reliable and accurate adjustment, in particular millimetric adjustment, so as to enable accurate adjustment of the optimum position of the orthosis. In addition, the adjustment must be lockable so as to avoid any loss of adjustment, in particular while sleeping.

Currently, there do not exist any pre-fabricated orthoses having volume, retention quality, and adjustability that are comparable to devices that are made-to-measure in a laboratory.

OBJECT AND SUMMARY OF THE INVENTION

An object of the present invention is to provide an intraoral orthosis that does not have the above-mentioned drawbacks.

In particular, an object of the present invention is to provide an intraoral orthosis that is simple, accurately adjustable, compact, comfortable, retentive, comparable to a made-to-measure orthosis but inexpensive to fabricate and to use.

More particularly, an object of the present invention is to provide an intraoral orthosis that may be easily adapted to each user and adjusted in accurate and simple manner, i.e. without any special instrument.

The present invention thus provides an intraoral orthosis comprising a first shell and a second shell, said shells being connected together by an adjustable connection device, said adjustable connection device comprising two notched tabs that are arranged respectively on either side of one of the shells, each notched tab co-operating in adjustable manner with a respective adjustment housing, arranged correspondingly on either side of the other of said shells, each notched tab having adjustment teeth to adjust the position of the shells one relative to the other, and locking housings to lock said position, said locking housings being oriented transversally relative to said adjustment teeth.

Advantageously, each adjustment housing includes at least one adjustment tooth adapted to co-operate with at least one respective adjustment tooth of the corresponding notched tab, so as to define a position of the first shell relative to the second shell.

Advantageously, one of said first and second shells is a mandibular shell, said adjustable connection device being adapted to define the relative position of the two shells between a pushed back position and an advanced position of said mandibular shell.

Advantageously, said adjustable connection device limits the opening of the mouth while the orthosis is being used.

Advantageously, the shells are made by molding and/or folding.

Advantageously, the shells are made of a material that is relatively flexible, such as polypropylene or Rilsan®, making it possible to adapt each shell to the corresponding dental arch.

Advantageously, the adjustment housings are molded integrally with their respective shell, each adjustment housing being connected to said shell by a foldable support structure.

Advantageously, each adjustment housing includes a locking system.

Advantageously, said locking system comprises a locking element that is movable relative to said adjustment housing between a locked position in which locking projections of the locking element co-operate with locking housings of said notched tab, and an unlocked position in which said locking projections do not co-operate with said locking housings.

Advantageously, said locking projections and housings are in the shape of complementary grooves.

Advantageously, said locking element includes at least one shoulder that co-operates with said adjustment housing in the unlocked position, so as to prevent said locking element from being removed from said adjustment housing.

Advantageously, said locking element includes at least one bead that co-operates with said adjustment housing while said locking element is moving between its locked and unlocked positions, so as to create resistance to movement and thus prevent any unwanted movement.

Advantageously, each shell includes a respective imprint element that is made of a thermoformable material for matching the shape of the user's teeth, each imprint element being fastened to its respective shell by being molded therein.

Advantageously, the imprint elements are made of a material that is substantially rigid at ambient temperature and substantially deformable when heated.

Advantageously, the imprint elements are made of a material that is selected from the family of polycapronolactones (PCL), such as CAPA®.

Advantageously, said shells include fastener profiles, such as ribs, grooves, or projections for improving the fastening of the imprint elements while they are being molded.

The present invention also provides a method of fabricating an orthosis as described above, said method comprising the following steps: molding the maxillary and mandibular shells; molding the imprint elements in said shells; fabricating the adjustable connection device, in particular by folding at least one portion of at least one shell; and assembling the shells at the adjustable connection device.

The present invention also provides a method of adjusting an orthosis fabricated in accordance with the above-described method, the adjustment method comprising the following steps: heating the imprint elements to a working temperature in which the imprint elements are deformable; putting the orthosis with its heated imprint elements into place in the user's mouth so as to form splints by imprinting the user's teeth in the imprint elements; cooling said imprint elements; and adjusting the relative position of the maxillary and mandibular shells by means of the adjustable connection device.

BRIEF DESCRIPTION OF THE DRAWINGS

These characteristics and advantages of the present invention, and others, appear more clearly from the following detailed description of an advantageous embodiment thereof, given by way of non-limiting example, and with reference to the accompanying drawings, in which.

MORE DETAILED DESCRIPTION

With reference to the drawings, the orthosis of the present invention comprises a first shell 10 and a second shell 20. One of the two shells is the maxillary shell, and the other shell is the mandibular shell. In the figures, the maxillary shell 10 is shown as being the top shell, and the mandibular shell 20 is shown as being the bottom shell. Each shell presents a shape that is rounded and hollow and that is made of a material that is relatively flexible, such as polypropylene or Rilsan®, so as to make it possible to adapt the shells to dental arches of any size. Advantageously, the shells are made mainly by molding.

The two shells are connected together by an adjustable connection device 30.

Figure 6:
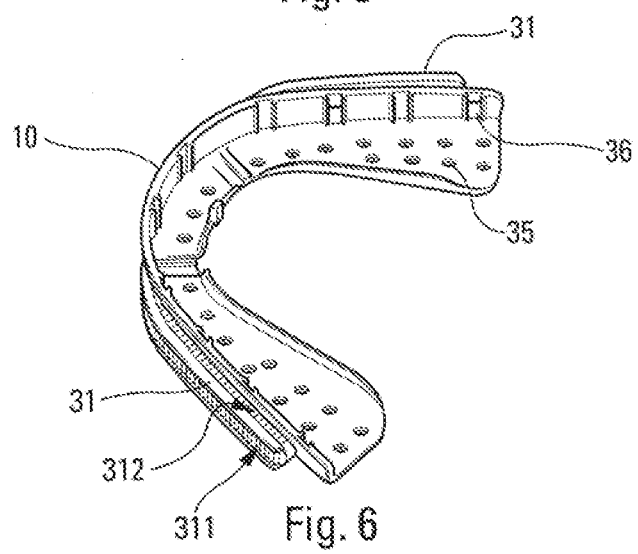
FIG. 6 is view of a detail of a maxillary shell.

As shown in the figures, the connection device includes two notched tabs 31, with a respective notched tab 31 being arranged on each side of one shell of the orthosis, e.g. the maxillary shell 10 as shown in FIG. 6. The other shell, in this configuration the mandibular shell 20, thus includes two adjustment housings 32 that each receive a notched tab 31 so as to define accurately the position of the mandibular shell 20 relative to the maxillary shell 10.

Figure 8:
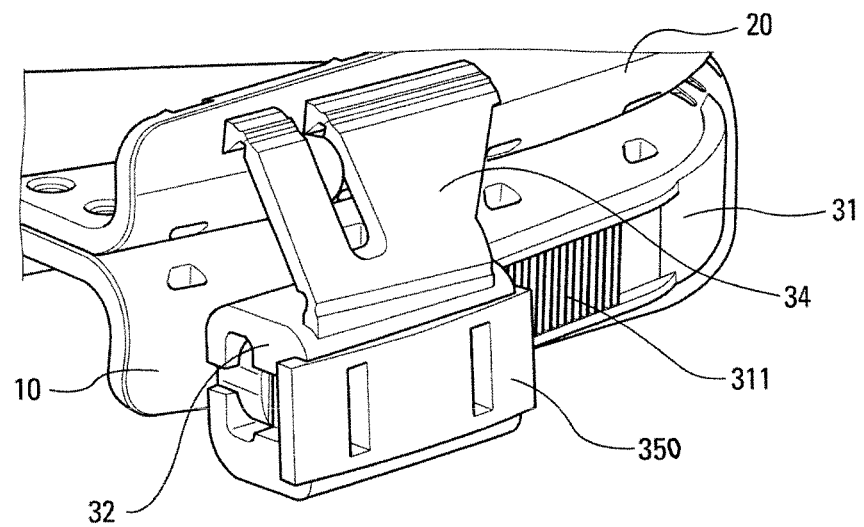
FIG. 8 is a diagrammatic perspective view of an orthosis with both shells assembled together, in an advantageous variant of the invention.

Naturally, the adjustable connection device could be reversed, i.e. with the notched tabs could be arranged on the mandibular shell and the adjustment housings on the maxillary shell, as shown in FIG. 8, for example.

Figure 9:
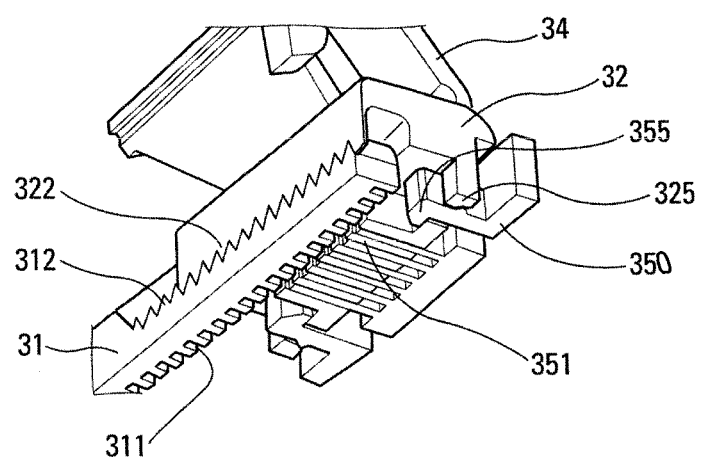
FIG. 9 is a view of a detail of the adjustment system for adjusting the FIG. 8 orthosis.

As can be seen in FIG. 9, each adjustment housing 32 includes at least one adjustment tooth 322, specifically in this example a plurality of adjustment teeth 322 that come to co-operate with at least one adjustment tooth 312, specifically in this example a plurality of adjustment teeth 312 of the notched tabs 31, so as to adjust accurately the position of the orthosis. Preferably, the adjustment teeth 312 and 322 are of shapes that are complementary, e.g. triangular, as can be seen in FIG. 9. Preferably, the teeth 312 of the notched tabs 31 are oriented axially, i.e. vertically in the position of the orthosis shown in FIGS. 1 to 4 and 8. It should be observed that the adjustment teeth 312 and 322 may be of any number, shape, and orientation.

Figure 7:
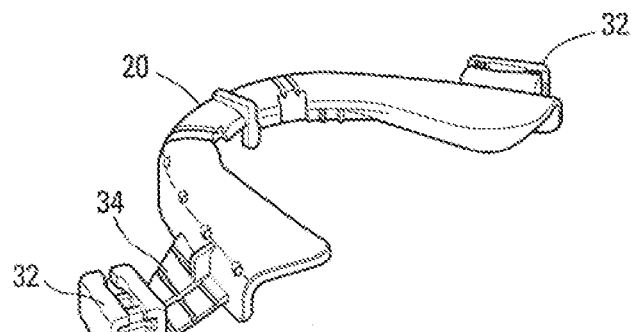
FIG. 7 is view of a detail of a mandibular shell.

The second shell 20 shown in FIG. 7 includes two adjustment housings 32 that are connected to the second shell 20 by respective foldable support structures 34. The second shell 20 with its support structures 34 and its adjustment housings 32 may thus be made by molding and folding. The method of fabricating the orthosis is thus particularly simple and does not require any complex manipulation.

When the adjustment housing 32 is folded in its working position, in order to assemble the mandibular shell to the maxillary shell, it suffices to insert the notched tabs 31 in said housings 32 and to adjust the position of the orthosis accurately, by causing said notched tabs to advance and/or to push back in said adjustment housings 32. The adjustable connection device 30 thus advantageously functions like a clamping collar used for fastening cables, for example.

A locking system advantageously makes it possible to block the position that is deemed to be effective for each patient. FIGS. 9 to 12 show advantageous embodiments of the locking system. In these examples, each adjustment housing 32 includes a locking element 350 that comprises at least one, and preferably a plurality of locking projections 351, adapted to co-operate with locking housings 311 provided on each notched tab 31.

Preferably, the locking housings 311 are formed by grooves that are oriented transversally, in particular perpendicularly, relative to the axial orientation of the teeth 311.

As can be seen in FIGS. 9 to 12, the locking projections and housings have groove shapes that are complementary. The locking element 350 is movable relative to its respective adjustment housing 32, between a locked position visible in FIGS. 10 and 12, and an unlocked position visible in FIGS. 9 and 11. Advantageously, the locking element 350 includes a shoulder 355 that co-operates with an abutment 325 in the unlocked position. This prevents the locking element 350 from being removed accidentally from its adjustment housing 32. Advantageously, the locking element 350 also includes a bead 356 that co-operates with a flange 326 of the adjustment housing 32, said bead being below said flange in the locked position, and above said flange in the unlocked position. This makes it possible to create resistance to moving the locking element 350, so as to avoid any unwanted unlocking.

Figure 10:
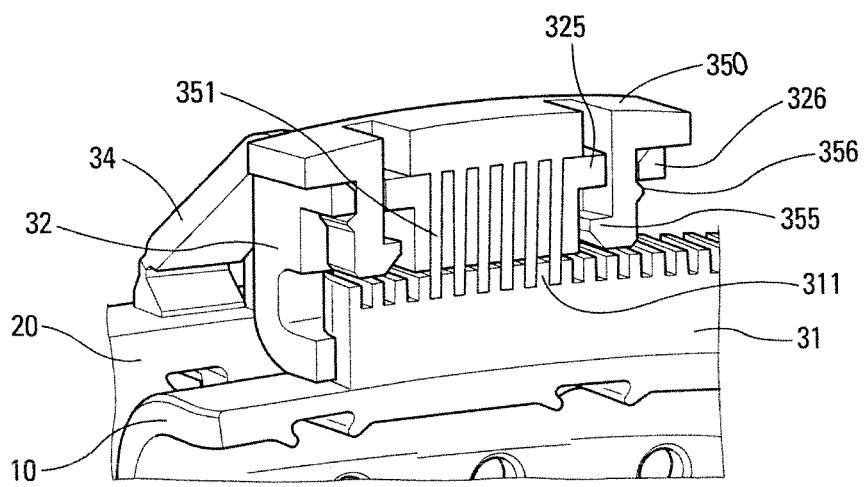
FIGS. 10 and 11 are views of a detail of the locking system for locking the FIG. 8 orthosis, respectively in the locked and unlocked positions.
Figure 11:
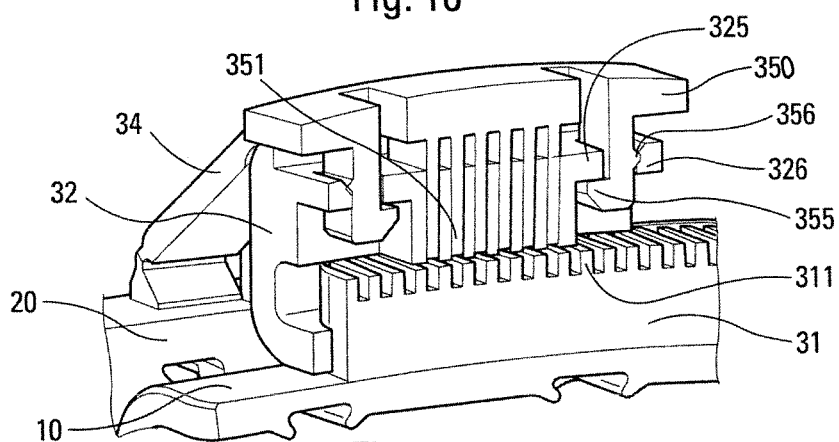
Figure 12:
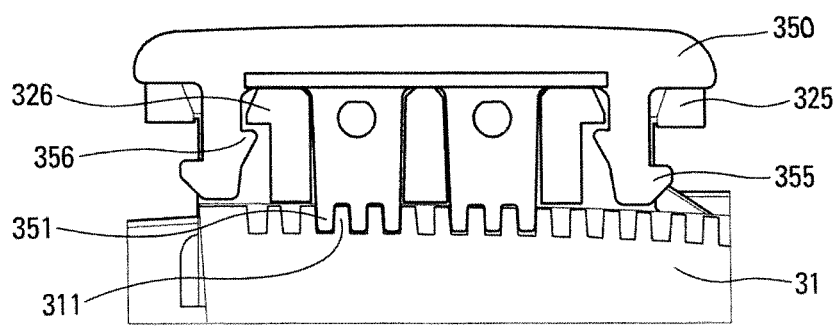
FIG. 12 is a diagrammatic view of a variant of the locking system, in the locked position.

In the variant in FIGS. 10 and 11, the locking element 350 includes two inwardly-directed shoulders 355, and two outwardly-directed beads 356. In the variant in FIG. 12, there are two outwardly-directed shoulders 355, and two inwardly-directed beads 356. In general, the shoulders 355 and the beads 356 may be of any number, shape, and orientation.

FIG. 6 shows a preferred embodiment of the notched tabs 31. In this variant, each notched tab 31 is formed by a bar portion that extends along one side of the shell 10, said bar portion including the locking housings 311 on its outside face. The bar portion is connected to said shell 10 by a smallsized bridge of material such that, in cross-section, said notched tab is approximately T-shaped, extending sideways from the shell 10. On its top surface (in the position in FIG. 6) or on its bottom surface, the bridge of material includes adjustment teeth 312. The adjustment teeth thus extend in a direction that is approximately perpendicular to the locking housings 311.

FIG. 7 shows a preferred embodiment of the adjustment housings 32 that are adapted to co-operate with the notched tabs of FIG. 6. In this variant, each adjustment housing comprises a hollow casing in which a notched tab may slide. The hollow casing defines a longitudinal slot in which the bridge of material of the notched tab passes, with a side edge of said slot including the adjustment teeth 322 that are adapted to co-operate with the adjustment teeth 311. The outer face of the hollow casing includes openings making it possible to assemble the locking element 35.

Figure 1:
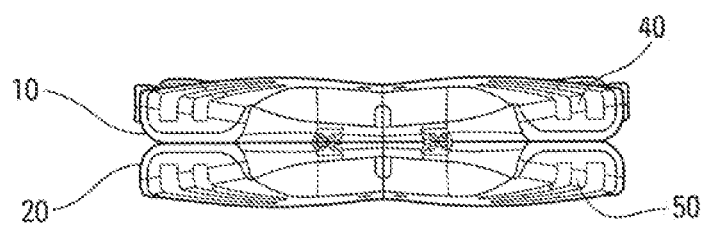
FIG. 1 is a rear cross-section view of an orthosis in an advantageous embodiment of the present invention, in a position in which the two shells are superposed.
Figure 2:
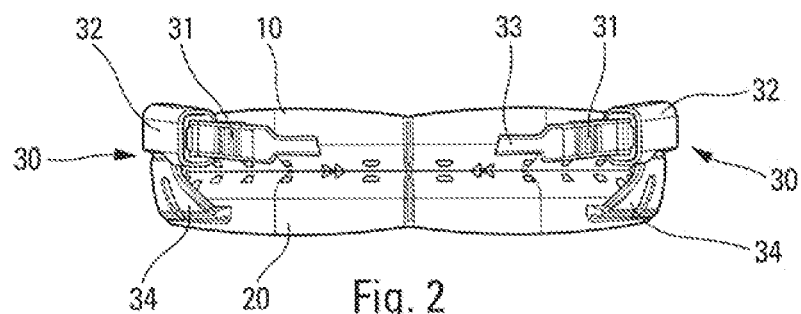
FIG. 2 is a front cross-section view of the FIG. 1 orthosis, in said superposed position.
Figure 3:
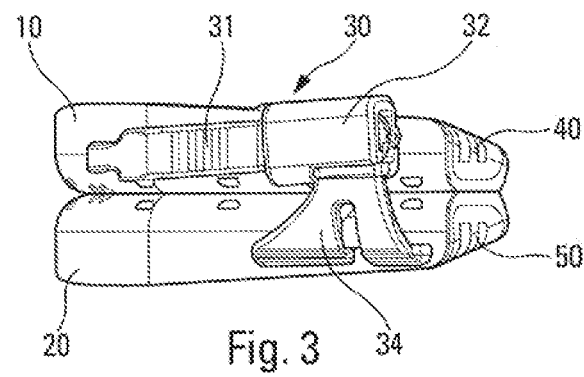
FIG. 3 is a side cross-section view of the FIGS. 1 and 2 orthosis, still in the superposed position.
Figure 4:
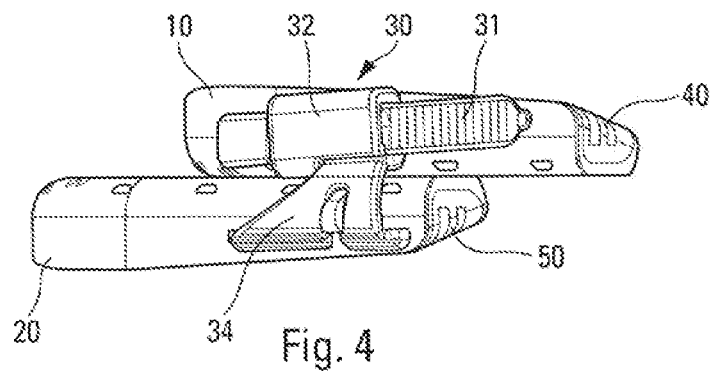
FIG. 4 is a view similar to the view in FIG. 3, with the mandibular shell in an advanced position.
Figure 5:
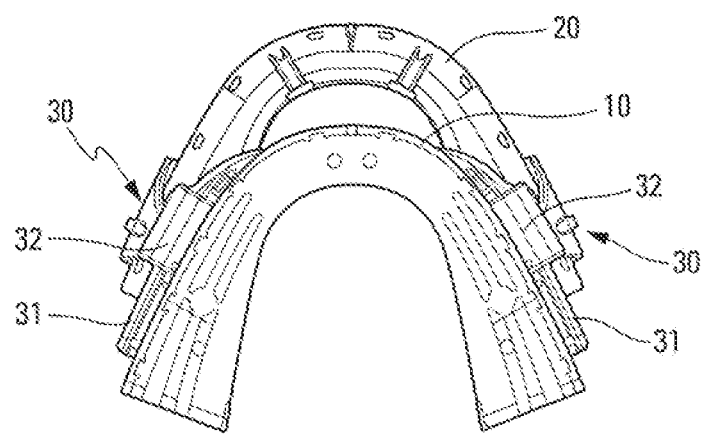
FIG. 5 is a plan view of the FIG. 4 orthosis.

FIGS. 3 and 4 show two extended adjustment positions with, in FIG. 3, the shells being superposed, corresponding to the pushed back position of the mandibular shell, and, in FIG. 4, the mandibular shell being in its advanced position.

The invention thus enables the adjustment of the orthosis to be accurate, in particular to be millimetric, without any need for an instrument, and, if necessary, with the possibility of adjusting the two sides asymmetrically. The adjustment can be modified at will without damaging the system, the locking system avoiding any spontaneous and/or unwanted change in position.

Advantageously, the adjustable connection device 30 exerts stress that limits the opening of the mouth, where said opening of the mouth is known for being detrimental to the satisfactory action of the mandibular propulsion device. Thus, this also improves the effectiveness of the orthosis in use.

The adjustable connection device 30 possesses a hinge that is associated with folding of the support structures 34, and this makes it possible to accept limited sideways movements of the shells 10, 20, improving comfort, but without that allowing the mandibular shell to be pushed back.

In another advantageous aspect, in each shell 10, 20, the orthosis of the invention includes an imprint element made of a thermoformable material, i.e. a material that becomes deformable when heated. Materials of this type, that are substantially rigid at ambient temperature and substantially deformable when heated, include in particular materials from the family of polycapronolactones (PCL), and in particular CAPA®. In a particularly advantageous aspect, the imprint elements 40, 50 are fastened in their respective shells 10, 20 by being molded therein. Thus, no adhesive, connection, or other layer is necessary between the imprint element and the shell. The fabrication of the orthosis is thus simplified.

In order to improve the fastening of the elements to the shells, the shells 10, 20 advantageously include fastener profiles 35, 36, such as ribs, grooves, and projections, for example. FIG. 6, which shows the first shell 10, shows examples of such fastener profiles, and similar profiles are advantageously provided in the second shell 20. The fastener profiles make it possible to reinforce the fastening of the imprint elements while they are being molded in the shells.

The use of imprint elements made of polycapronolactone is advantageous since it makes it possible for the user to take an imprint of his or her own teeth after heating the orthosis. Typically, the heating temperature does not exceed 50° C., so as to avoid any risk of injury, and the user then puts the orthosis with the heated imprint elements into the mouth so as to make an imprint of the teeth, and thus form two splints, one for each dental arch. After cooling, the imprint remains substantially non-deformable at ambient temperature, and thus guarantees that the orthosis fits the user's mouth closely while it is being used. Thus, after making the mold of the teeth, the user can use the orthosis very easily by adjusting the position of the second shell 20 relative to the first shell 10 by using the adjustable connection device 30.

The present invention thus makes it possible to provide an intraoral orthosis that may be fabricated easily and at little cost, and that may be available in retail outlets, each user being easily able to make the orthoses fit the mouth by taking an imprint of the teeth and by adjusting the position of the orthosis. No complex manipulation is necessary to achieve such fitting and adjustment. The device of the invention is thus usable by a large number of users because of its simplicity in use and its low cost. It should be observed that the notching system could be used on splints made in traditional manner, i.e. in a laboratory, for certain patients whose teeth require it.

Although the present invention is described above with reference to various advantageous embodiments thereof, naturally the invention is not limited to those embodiments, but on the contrary, any useful modification may be applied by a person skilled in the art, without going beyond the ambit of the present invention, as defined by the accompanying claims.

What is claimed is:

1. An intraoral orthosis comprising a first shell and a second shell, said shells being connected together by an adjustable connection device, wherein said adjustable connection device comprises two notched tabs that are arranged respectively on either side of one of the shells, each notched tab co-operating in adjustable manner with a respective adjustment housing, arranged correspondingly on either side of the other of said shells, each notched tab having adjustment teeth to adjust the position of the shells one relative to the other, wherein each adjustment housing includes a locking system comprising a locking element that is movable relative to said adjustment housing between a locked position in which locking projections of the locking element co-operate with locking housings of said notched tab, and an unlocked position in which said locking projections do not co-operate with said locking housings said locking housings being oriented transversally relative to said adjustment teeth.

2. An orthosis according to claim 1, wherein each shell includes a respective imprint element that is made of a thermoformable material for matching the shape of the user's teeth, each imprint element being fastened to its respective shell by being molded therein.

3. An orthosis according to claim 2, wherein the imprint elements are made of a material that is substantially rigid at ambient temperature and substantially deformable when heated.

4. An orthosis according to claim 3, wherein the imprint elements are made of a material that is selected from the family of polycapronolactones.

5. An orthosis according to claim 2, wherein said shells include fastener profiles for improving the fastening of the imprint elements while being molded.

6. The orthosis according to claim 2, wherein said shells include fastener profiles that are ribs, grooves, or projections for improving the fastening of the imprint elements while they are being molded.

7. An orthosis according to claim 1, wherein the shells are made by molding and/or folding.

8. An orthosis according to claim 7, wherein the shells are made of a material that is relatively flexible so that each shell is adaptable to the corresponding dental arch.

9. The orthosis according to claim 7, wherein the shells are made of polypropylene or polyamide 11 so that each shell is adaptable to a corresponding dental arch.

10. A method of fabricating an orthosis according to claim 1, said method comprising the following steps: providing said shells by molding maxillary and mandibular shells; molding imprint elements in said shells; fabricating the adjustable connection device; and assembling the shells at the adjustable connection device.

11. A method of adjusting an orthosis fabricated in accordance with the method of claim 10, the adjustment method comprising the following steps: heating the imprint elements to a working temperature in which the imprint elements are deformable; putting the orthosis with the heated imprint elements in place in the user's mouth so as to form splints by imprinting the user's teeth in the imprint elements; cooling said imprint elements; and adjusting the relative position of the maxillary and mandibular shells by the adjustable connection device.

12. An orthosis according to claim 1, wherein each adjustment housing includes at least one adjustment tooth adapted to co-operate with at least one respective adjustment tooth of the corresponding notched tab, so as to define a position of the first shell relative to the second shell.

13. An orthosis according to claim 1, wherein one of said first and second shells is a mandibular shell, the relative position of the two shells being adjustable between a pushed back position and an advanced position of said mandibular shell.

14. An orthosis according to claim 1, wherein the adjustment housings are molded integrally with their respective shell, each adjustment housing being connected to said shell by a foldable support structure.

15. An orthosis according to claim 1, wherein said locking projections and housings are in the shape of complementary grooves.

16. An orthosis according to claim 1, wherein said locking element includes at least one shoulder that co-operates with said adjustment housing in the unlocked position, so as to prevent said locking element from being removed from said adjustment housing.

17. An orthosis according to claim 1, wherein said locking element includes at least one bead that co-operates with said adjustment housing while said locking element is moving between its locked and unlocked positions, so as to create resistance to movement and thus prevent any unwanted movement.

18. A method of fabricating an orthosis according to claim 1, said method comprising the following steps: providing said shells by molding maxillary and mandibular shells; molding imprint elements in said shells; fabricating the adjustable connection device by folding at least one portion of at least one shell; and assembling the shells at the adjustable connection device.

* * * * *